(12) United States Patent (10) Patent No.: US 6,414,185 B2
Kleiner (45) Date of Patent: Jul. 2, 2002

(54) ALUMINUM SALTS OF PHOSPHINIC ACIDS

(75) Inventor: Hans-Jerg Kleiner, Kronberg (DE)

(73) Assignee: Ticona GmbH (DE)

( * ) Notice: Subject to any disclaimer, the term of this patent is extended or adjusted under 35 U.S.C. 154(b) by 0 days.

(21) Appl. No.: 09/824,478

(22) Filed: Apr. 2, 2001

Related U.S. Application Data

(62) Division of application No. 09/214,473, filed as application No. PCT/EP97/03631 on Sep. 7, 1997, now Pat. No. 6,211,402.

(30) Foreign Application Priority Data

Jul. 22, 1996 (DE) .......................................... 196 29 432

(51) Int. Cl.$^7$ .................................................. C07F 9/30
(52) U.S. Cl. ............................................. 562/8; 562/20
(58) Field of Search ................................. 562/8, 20, 22

(56) References Cited

U.S. PATENT DOCUMENTS 4,810,425 A * 3/1989 Nelson

OTHER PUBLICATIONS

CA:72:79173 abs of J. Polym. Sci. Par A–1 by Flagg et al 8(1) pp 1–14 (1981).*
CA:95:17327 abs of Mikulski et al Transition Met. Chem. (Weinheim, Ger.) 6(2) pp 79–82 1981.*
CA:96:181429 abs of EP 38778 Oct. 1981.*
CA:124:318847 abs of EP699708 Mar. 1996.*
CA:76:132457 abs of Izv. Akad. Nauk SSSR, Neorg. Mater. 8(3) pp 433–438 1972.*
CA:45:2552 abs of Doklady Akad. Nauk S.S.S.R. by Kolmogorov et al 65 pp 681–684 1949.*
CA:75:152373 abs of DE 2102841 Aug. 1971.*

* cited by examiner

Primary Examiner—Jean F. Vollano
(74) Attorney, Agent, or Firm—Connolly Bove Lodge & Hutz LLP

(57) ABSTRACT

Aluminum salts of phosphinic acid or diphosphinic acids having alkyl and/or aryl substitutes, obtainable by heating an ester of the corresponding phosphinic acids or diphosphinic acids with aluminum hydroxide at a temperature of more than 150° C. under pressure in the presence of water, are distinguished by a particular crystal structure and are suitable as flameproofing agents for plastics.

21 Claims, No Drawings

ALUMINUM SALTS OF PHOSPHINIC ACIDS

RELATED APPLICATIONS

This is a divisional application of Ser. No. 09/214,473 filed Feb. 16, 1999 which issued as U.S. Pat. No. 6,211,402 which is a 371 of PCT/EP97/03631, filed Sep. 7, 1997, WO 98/03515.

The invention relates to aluminum salts of phosphinic acids, processes for their preparation and to their use as flameproofing agents.

Aluminum salts of phosphinic acids are valuable flameproofing agents for polyester and polyamide molding materials. They are prepared from the phosphinic acids in aqueous solution with metal carbonates, metal hydroxides or metal oxides (EP-A2-0699708).

To date, phosphinic esters have been converted into the corresponding phosphinic acids in good yields on hydrolysis at 180° C. under pressure with excess water only when the alcohol formed is removed as a mixture with water from the gas phase of the autoclave (Houben-Weyl, Methoden der organischen Chemie [Methods of organic chemistry] 1982, Volume E2, page 142; DE-A1-27 45 982).

It was found that the aluminum salts of phosphinic acids can be prepared in good yields under pressure from the corresponding esters with water and aluminum hydroxide. Furthermore, it was found that the aluminum salts of phosphinic acids or diphosphinic acids having alkyl and/or aryl substitutes are formed in a novel crystal form at a temperature above 150° C. under pressure. These aluminum salts are defined as a high-temperature modification. The aluminum salts known to date and prepared at temperatures of 80 to 100° C. are defined as a low-temperature modification.

The invention thus relates to aluminum salts of phosphinic acids or diphosphinic acids having alkyl and/or aryl substituents, obtainable by heating an ester of the corresponding phosphinic acids or diphosphinic acids with aluminum hydroxide at a temperature of more 150° C. under pressure in the presence of water.

The invention also relates to aluminum salts of phosphinic acids or diphosphinic acids having alkyl and/or aryl substituents, obtainable by heating the corresponding aluminum salts in the low-temperature modification at a temperature of more than 150° C. under pressure in the presence of water.

Alkyl substituents are preferably $C_1$–$C_8$-alkyl, in particular $C_1$–$C_4$-alkyl, linear or branched, for example methyl, ethyl, n-propyl, isopropyl, isobutyl, n-butyl, n-hexyl or n-octyl. A preferred aryl substituent is the phenyl group.

The aluminum salts of the high-temperature modification may also be polymers of the phosphinic acid or disphosphinic acids. The terms "phosphinic acid" and "diphosphinic acid", accordingly, include monomers, oligomers and polymers.

The invention furthermore relates to a process for the preparation of aluminum salts of phosphinic acids or diphosphinic acids, esters of the corresponding phosphinic acids or diphosphinic acids being reacted with aluminum hydroxide under pressure at 150 to 350° C. in the presence of water.

The invention furthermore relates to a process for the preparation of aluminum salts of phosphinic acids or diphosphinic acids of the high-temperature modification, the corresponding aluminum salts in the low-temperature modification being exposed to a temperature in the range of 150 to 350° C. in the presence of water.

Suitable aluminum salts of phosphinic acids or diphosphinic acids are, for example, compounds according to the formula I or II

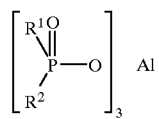

(I)

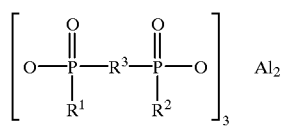

(II)

in which $R^1$, $R^2$ are $C_1$–$C_8$-alkyl, preferably $C_1$–$C_4$-alkyl, linear or branched, e.g. methyl, ethyl, n-propyl, isobutyl, n-butyl, n-hexyl, phenyl $R^3$ is $C_1$–$C_{10}$-alkylene, linear or branched, e.g. methylene, ethylene, n-propylene, isopropylene, n-butylene, n-decylene, an arylene, e.g. phenylene, napthylene;

alkylarylene, e.g. methylphenylene, ethylphenylene, methylphenylenemethyl;

arylalkylene, e.g. phenylmethylene, phenylethylene.

The aluminum salts according to the formula I or II can be prepared, for example, from phosphinic esters or diphosphinic esters of the formula III or IV

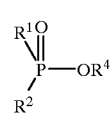

(III)

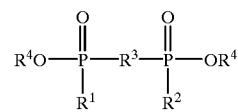

(IV)

in which $R^1$, $R^2$ and $R^3$ have the abovementioned meaning and $R^4$ is $C_1$–$C_8$-alkyl, preferably $C_4$–$C_6$-alkyl. Advantageously, the compounds according to the formula III or IV are reacted with water and aluminum hydroxide under pressure at 150 to 350° C. and heated for several hours in this temperature range, the corresponding aluminum salts being obtained as the high-temperature modification.

Particularly suitable starting materials for the preparation of the aluminum salts are: methyl dimethylphosphinate, ethyl ethylmethylphosphinate, isobutyl ethymethyl phosphinate, n-butyl methylpropyl phosphinate, amyl isobutylmethyl phosphinate, isopropyl hexylmethyl phosphinate, n-butyl methyloctyl phosphinate, n-butyl methylphenylphosphinate, n-pentyl diphenylphosphinate, di-n-butyl hexane-1,6-di(methylphosphinate) and diisobutyl benzene-1,4-di(methylphosphinate).

The process for the preparation of the high-temperature modification is carried out in a variant in such a way that phosphinic esters are heated with excess water and stoichiometric amounts of aluminum hydroxide under pressure to 150 to 350° C., preferably 180 to 250° C., expediently with continuous stirring. The required reaction times are in general at least 4 and preferably at least 40 hours, in particular 50 to 70 hours. The reaction times are dependent on the chain length of the ester group (for example, $R^4$ in the formulae III and IV). Methyl esters hydrolyze, for example, more rapidly than the butyl esters. After the end of the reaction, the resulting crystals are isolated and dried. The reaction conditions, such as temperature and reaction time, can also be varied so that mixtures of low-temperature modification and high-temperature modification are obtained.

Aluminum salts of the high-temperature modification are gradually transformed at room temperature into the low-temperature modification, but the crystal habit of the high-temperature modification is retained.

The high-temperature modification consists of acicular crystals which have a fibrous appearance. The crystals generally have a width in the range from about 0.2 to 1.5 µm, in particular 0.2 to 1 µm. The ratio of width to length of the crystal has, as a rule, a value of less than 0.2. The ratio of width to length of the crystal is usually about 0.1 or less. The crystals usually form agglomerates which have the appearance of felt-like bales. The agglomerates are obtained with a diameter in the size range from about 10 to 170 µm, the main proportion comprising agglomerates having a diameter of about 20 µm.

The low-temperature modification consists of cylindrical crystals which as a rule have a width of more than 1.5 µm, typically 2 to 5 µm. The ratio of width to length of the crystals is usually in the range from 0.6 to 2, typically 2. The crystals also form agglomerates which for the most part have a diameter of about 20 µm.

The high-temperature modification of the aluminum salts is particularly suitable as flameproofing agents or flame retardants for plastics, in particular for polyester or polyamide.

The aluminum salts of the high-temperature modification have advantages for use as flameproofing agents for plastics. Investigations have shown that the flame-retardant effect of the salts of the phosphinic acids in the plastic depends on the particle size of the salt and that an optimum particle size results. The aluminum salts of the high-temperature modification form directly in the advantageous particle size. Milling of the aluminum salts is therefore not necessary for compounding, which means an economic advantage for the preparation of flameproofed plastics. In addition, the finer structure of the aluminum salt permits a more homogeneous distribution of the flameproofing agent in the plastic. The fibrous structure of the aluminum salt moreover leads to reinforcement of the plastic (fiber reinforcement). The finer structure leads to a larger surface area of the particle and, for example with the use of synergistic agents, such as nitrogen compounds, improves their flameproofing effect.

EXAMPLE 1

308 g (1.75 mol) of n-butyl methyl-n-propylphosphinate, 290 ml of water and 45.5 g (0.583 mol) of aluminum hydroxide are introduced into a 1 l autoclave and kept at 200° C. for 50 hours while stirring. Cooling and filtration with suction are then carried out, followed by drying. 214 g of aluminum salt of methyl-n-propylphosphinic acid are obtained. This corresponds to a yield of 94% of theory. The product does not melt up to 360° C. The product retains the crystal habit of a high-temperature modification (pseudomorphism).

If the product is prepared according to EP-A2-0699708, it is obtained in the low-temperature modification (in this context, also see the attached tables showing the maxima of X-ray diffraction patterns, Cu—$K\alpha_1$).

EXAMPLE 2

264 g (1.5 mol) of n-butyl ethylmethylphosphonate, 250 ml of water and 39 g (0.5 mol) of aluminum hydroxide are kept at 200° C. in a 1 l autoclave for 50 hours while stirring. Cooling and filtration with suction are then carried out, followed by drying at 100° C. in a vacuum drying oven. 157 g of aluminum salt of ethylmethylphosphinic acid, having a residual water content of 58 ppm and a mean particle size of 20.03 µm, are obtained. This corresponds to a yield of 90% of theory. The product does not melt up to 360° C. The product retains the crystal habit of a high-temperature modification (pseudomorphism).

If the product is prepared according to Patent EP-A2-0699708, it is obtained in the low-temperature modification (in this context, also see the attached tables showing the maxima of X-ray diffraction patterns, Cu—$K\alpha_1$).

EXAMPLE 3

213 g (1.2 mol) of amyl ethylmethylphosphinate, 200 ml of water and 31.2 g (0.4 mol) of aluminum hydroxide are kept at 190 to 220° C. in a 1 l autoclave for 50 hours. Filtration with suction and drying are then carried out. 123 g of aluminum salt of ethylmethylphosphinic acid are obtained. This corresponds to a yield of 88.5% of theory. The product is obtained in the crystal habit of a high-temperature modification (in this context, see Example 1).

TABLE 1

X-ray diffraction pattern of aluminum methylpropylphosphinate (Debye-Scherrer beam path, Cu—$K\alpha_1$, transmission)

| Low-temperature phase | | High-temperature phase | |
| --- | --- | --- | --- |
| 2θ [°] | rel. int. | 2θ [°] | rel. int. |
| 8.75 | 100 | 8.35 | 100 |
| 14.10 | 1 | | |
| 15.20 | 2 | 14.55 | 2 |
| 16.60 | 3 | | |
| 20.25 | 6 | 20.05 | 6 |
| 20.75 | 7 | | |
| 22.10 | 3 | 22.05 | <1 |
| 22.50 | 4 | | |
| 23.90 | 3 | 23.40 | 2 |
| 26.85 | 3 | 26.30 | 2 |
| 27.30 | 2 | | |
| 28.70 | 1 | | |
| 29.65 | 2 | 28.95 | <1 |
| 30.10 | 2 | | |
| 33.50 | 1 | 32.45 | <1 |

TABLE 2

X-ray diffraction pattern of aluminum ethylmethylphosphinate (Debye-Scherrer beam path, Cu—$K\alpha_1$, transmission)

| Low-temperature phase | | High-temperature phase | |
| --- | --- | --- | --- |
| 2θ [°] | rel. int. | 2θ [°] | rel. int. |
| 9.70 | 100 | 9.35 | 100 |
| 19.60 | 20 | 18.95 | 9 |
| | | 19.55 | 5 |
| 25.95 | 4 | 25.45 | 2 |
| 27.75 | 13 | 26.70 | 5 |
| | | 27.15 | 2 |
| 32.70 | 2 | 31.70 | 1 |
| 34.20 | 1 | 32.60 | <1 |
| 35.45 | 3 | 34.20 | 1 |
| 36.95 | 1 | 35.50 | <1 |

EXAMPLE 4

250 g of aluminum salt of ethylmethylphosphinic acid, prepared at 90° C. according to Example 1 in EP-A2-

0699708 (low-temperature modification), are heated in 250 g of water for 50 hours at 200° C. The mixture is then allowed to cool to room temperature. The liquid is filtered off with suction and the crystals are dried. 230 g of aluminum salt of ethylmethylphosphinic acid are obtained in the crystal habit of the high-temperature modification.

EXAMPLE 5

Comparative Example 30 g of aluminum salt of ethylmethylphosphinic acid, prepared at 90° C. (low-temperature modification), are stirred under a nitrogen atmosphere for 7 hours at 250° C. There is virtually no transformation into the high-temperature modification.

What is claimed is:

1. Aluminum methylpropylphosphinate, wherein the Cu—K$\alpha_1$ X-ray diffraction pattern has the following reflections at 2θ: 8.35, 14.55, 20.55, 22.40, 23.40, 26.30, 28.95, and 32.45°.

2. Aluminum ethylmethylphosphinate, wherein the Cu—K$\alpha_1$ X-ray diffraction pattern has the following reflections at 2θ: 9.35, 18.95, 19.55, 25.45, 26.70, 27.15, 31.70, 32.60, 34.20 and 35.50°.

3. Crystals which are a high temperature modification of an aluminum salt of a phosphinic acid or diphosphinic acid having substituents that are a) alkyl, b) aryl, or c) mixture of alkyl and aryl, with a fibrous needle shape form, which are formed above 150° C. under pressure in the presence of water and having at least two alkyl substituents with at least one substituent as either ethyl or propyl.

4. The crystals as claimed in claim 3, wherein said substituents are $C_1$–$C_8$ alkyl or phenyl.

5. The crystals as claimed in claim 3, wherein the substituents are $C_1$–$C_4$ alkyl.

6. The crystals as claimed in claim 3, wherein the substituents are methyl, ethyl, propyl, or phenyl.

7. The crystals as claimed in claim 3, wherein the crystals have a ratio of width to length of less than 0.2.

8. The crystals as claimed in claim 7, wherein said ratio of width to length of less than about 0.1

9. The crystals as claimed in claim 3, wheren the crystals have a width in the range from about 0.2 to 1.5 μm.

10. The crystals as claimed in claim 6, wherein the crystals have a ratio of width to length of less than 0.2.

11. The crystals as claimed in claim 10, wherein said ratio of width to length of less than about 0.1.

12. The crystals as claimed in claim 11, wherein the crystals have a width in the range of from about 0.2 to 1.5 μm.

13. A flame proofing agent for plastics which comprises the crystals as claimed in claim 3.

14. A flame proofing agent for plastics which comprises the crystals as claimed in claim 4.

15. A flame proofing agent for plastics which comprises the crystals as claimed in claim 5.

16. A flame proofing agent for plastics which comprises the crystals as claimed in claim 6.

17. A flame proofing agent for plastics which comprises the crystals as claimed in claim 1.

18. A flame proofing agent for plastics which comprises the crystals as claimed in claim 2.

19. The crystals as claimed in claim 3, wherein ssaid substituents have two alkyl substituents with at least one substituent as either ethyl or propyl.

20. The crystals as claimed in claim 19, wherein said at least one substituent is ethyl.

21. The crystals as claimed in claim 19, wherein said at least one subtituent is propyl.

* * * * *

UNITED STATES PATENT AND TRADEMARK OFFICE
CERTIFICATE OF CORRECTION

PATENT NO. : 6,414,185 B2 Page 1 of 1
DATED : July 2, 2002
INVENTOR(S) : Hans-Jerg Kliener It is certified that error appears in the above-identified patent and that said Letters Patent is hereby corrected as shown below:

<u>Column 5,</u>
Lines 18-19, delete "reflections" and insert -- reflexes --.
Line 19, delete "20.55, 22.40" and insert -- 20.05, 22.05 --.
Lines 22-23, delete "reflections" and insert -- reflexes --.

<u>Column 6,</u>
Line 28, delete "ssaid" and insert -- said --.

Signed and Sealed this

Fifteenth Day of October, 2002

*Attest:*

*Attesting Officer*

JAMES E. ROGAN
*Director of the United States Patent and Trademark Office*